(12) United States Patent
Masuda et al.

(10) Patent No.: US 7,345,161 B2
(45) Date of Patent: Mar. 18, 2008

(54) **DETECTION REAGENT FOR SHIGA TOXIN FAMILY GENE OF ENTERO-HEMORRHAGIC *ESCHERICHIA COLI***

(75) Inventors: Noriyoshi Masuda, Tokyo (JP); Kiyoshi Yasukawa, Kawasaki (JP); Ryuichi Horie, Zama (JP)

(73) Assignee: Tosoh Corporation, Shunan-shi (JP)

( * ) Notice: Subject to any disclaimer, the term of this patent is extended or adjusted under 35 U.S.C. 154(b) by 0 days.

(21) Appl. No.: 11/048,794

(22) Filed: Feb. 3, 2005

(65) Prior Publication Data

US 2006/0115823 A1    Jun. 1, 2006

(30) Foreign Application Priority Data

Feb. 3, 2004    (JP)    ............... 2004-026996

(51) Int. Cl.
    *C07H 21/04*    (2006.01)
    *C12Q 1/68*    (2006.01)
    *C12P 19/34*    (2006.01)

(52) U.S. Cl. .............. 536/24.3; 435/6; 435/91.2

(58) Field of Classification Search ............. None
    See application file for complete search history.

(56) References Cited

U.S. PATENT DOCUMENTS 6,080,400 A * 6/2000 Williams et al. ............. 424/93.2
2003/0008305 A1 * 1/2003 Maruyama et al. ............. 435/6

FOREIGN PATENT DOCUMENTS

DE    199 46 296 A1    3/2001
EP    1 236 806 A2    9/2002
EP    1 375 674 A1    1/2004
WO    WO 01/94634 A2    12/2001

OTHER PUBLICATIONS

Buck et al., Design strategies and performance of custom DNA sequencing primers. BioTechniques (1999) 27: 528-536.*
Product #1256, Random Primer 24, New England Biolabs Catalog (1998-1999), p. 121.*
CD-ROM containing an unbridged electronic version of the article on the "Preparation and Utilization of Isolated and Purified Oligonucleotides" by Dr. Andrew Chin.
Derwent Publications, AN 2004-233274, XP-002357559, JP 2004-081054, Mar. 18, 2004.
CD-ROM containing an unbridged electronic version of the article on the "Preparation and Utilization of Isolated and Purified Oligonucleotides" by Dr. Andrew Chin, Mar. 9, 2002.

* cited by examiner

*Primary Examiner*—Young J. Kim
*Assistant Examiner*—David C. Thomas
(74) *Attorney, Agent, or Firm*—Oblon, Spivak, McClelland, Maier & Neustadt, P.C.

(57) ABSTRACT

The present invention provides a combination of oligonucleotides preferable for composing a rapid and specific gene testing reagent for Shiga toxin family gene type 2 (stx) of entero-hemorrhagic *Escherichia coli* (EHEC). More specifically, the present invention provides a method for detecting stx2 RNA of EHEC by specifically amplifying only stx2 RNA using a primer having a sequence homologous or complementary to a base sequence specific for stx2 gene of EHEC and located at sites free of alterations between genotypes, and an oligonucleotide that binds to a specific site of stx2 RNA.

7 Claims, 4 Drawing Sheets

Fig.1

| GenBank X07865 | 521 | : CAAAATAATTTATATgTggCCgggTTCgTTAATACggCAA : | 560 |
| --- | --- | --- | --- |
| slt-II | 519 | : ---------------------A------------------ : | 558 |
| slt-IIv | 519 | : -g-------------------T--A--T----------A--- : | 558 |

`ACACCggCCCAAgCAATTATgCCgTT`

VT2-5F (SEQ ID NO:7) `TTCTACCgTTTTTCAgATTTTACAC`

| GenBank X07865 | 561 | : CAAATACTTTCTACCgTTTTTCAgATTTTACACATATATC : | 600 |
| --- | --- | --- | --- |
| slt-II | 559 | : ---------------------------------------- : | 598 |
| slt-IIv | 559 | : -------------A-A--------------g--------- : | 598 |

`gTTTATgAAAgAT` VT2-5S (SEQ ID NO:5)

| GenBank X07865 | 601 | : AgTgCCCggTgTgACAACggTTTCCATgACAACggACAgC : | 640 |
| --- | --- | --- | --- |
| slt-II | 599 | : ---------------------------------------- : | 638 |
| slt-IIv | 599 | : -T--------------TA---------------------- : | 638 |

VT2-12S (SEQ ID NO:10) `ACTgTTgCCTgTCg`

`ATACCACTCTgCAACgTgTCgCA` VT2-12F (SEQ ID NO:1,11)

| GenBank X07865 | 641 | : AgTTATACCACTCTgCAACgTgTCgCAgCgCTggAACgTT : | 680 |
| --- | --- | --- | --- |
| slt-II | 639 | : ---------------------------------------- : | 678 |
| slt-IIv | 639 | : ---------------------------------------- : | 678 |

`TCAATATggT`

| GenBank X07865 | 681 | : CCggAATgCAAATCAgTCgTCACTCACTggTTTCATCATA : | 720 |
| --- | --- | --- | --- |
| slt-II | 679 | : ---------------------------------------- : | 718 |
| slt-IIv | 679 | : ---------------------------------------- : | 718 |

`AAgTAgTAT`

| GenBank X07865 | 721 | : TCTggCgTTAATggAgTTCAgTggTAATACAATgACCAgA : | 760 |
| --- | --- | --- | --- |
| slt-II | 719 | : ---------------------------------------- : | 758 |
| slt-IIv | 719 | : ---------------------------------------- : | 758 |

`AgACCgCAATT` YO-VT2-S-G (SEQ ID NO:3)

| GenBank X07865 | 761 | : gATgCATCCAgAgCAgTTCTgCgTTTTgTCACTgTCACAg : | 800 |
| --- | --- | --- | --- |
| slt-II | 759 | : ---------------------------------------- : | 798 |
| slt-IIv | 759 | : --------A------------------------------- : | 798 |

`ACAgTgTC`

| GenBank X07865 | 801 | : CAgAAgCCTTACgCTTCAggCAgATACAgAgAATTTCg : 840 |
| --- | --- | --- | --- |
| slt-II | 799 | : ---------------------------------------- : | 838 |
| slt-IIv | 799 | : -----------g----------A----T------------ : | 838 |

`gTCTTCggAATg` VT2-7R (SEQ ID NO:2)

DETECTION REAGENT FOR SHIGA TOXIN FAMILY GENE OF ENTERO-HEMORRHAGIC ESCHERICHIA COLI

FIELD OF THE INVENTION

The present invention relates to a detection reagent for detecting entero-hemorrhagic *Escherichia coli* in clinical examinations, public health examinations, food evaluations and food poisoning examinations.

PRIOR ART

Shiga-toxin family (stx) is a potent toxin produced by entero-hemorrhagic *Escherichia coli* (EHEC) such as pathogenic *Escherichia coli* 0157. Major symptoms associated with infection by EHEC include watery stool followed by severe abdominal pain and bloody stool. In addition, some infected persons develop complications leading to hemolytic uremic syndrome (HUS) and encephalopathy, and this has been reported to cause death in the worst case.

Although the serotypes of EHEC are extremely varied, numbering more than 60 types, the most common serotype in terms of detection frequency is 0157:H7. In addition, stx is also broadly classified as type 1 (stx1) or type 2 (stx2) based on differences in antigenicity.

Although the 0157 antigen test and other tests are known methods for detecting and identifying EHEC, methods which detect a specific sequence present in the EHEC gene or RNA derived from said gene following the amplification of such a sequence are preferable in terms of sensitivity, speed and ease of procedure. A method that amplifies a target nucleic acid at a constant temperature is particularly preferable in terms of automation of a testing system.

DISCLOSURE OF THE INVENTION

A method for detecting and identifying EHEC had been reported in which an RNA derived from stx1 and stx2 is specifically amplified at a comparatively low temperature (41° C.) (Japanese Unexamined Patent Publication No. 2002-253257). In this method, an RNA amplification process is used, which process comprises the steps of producing a cDNA with an RNA-dependent DNA polymerase using a specific sequence of an RNA derived from stx1 or stx2 as a template, as well as a first primer having a sequence complementary to said specific sequence, and a second primer having a sequence homologous to said specific sequence, thereby forming a double-strand RNA-DNA, wherein the first primer or the second primer has a sequence in which a promoter sequence of an RNA polymerase is added to the 5' end of one of the primers, degrading the RNA of the double-strand RNA-DNA by ribonuclease H, thereby producing a single-strand DNA, and producing a double-strand DNA having the promoter sequence capable of transcribing the RNA composed of the RNA sequence or the sequence complementary to the RNA sequence with a DNA-dependent DNA polymerase using said single-strand DNA as a template, wherein said double-strand DNA produces an RNA transcription product in the presence of the RNA polymerase, and said RNA transcription product serves as a template for the subsequent cDNA synthesis with the RNA-dependent DNA polymerase. Moreover, the RNA amplification process is carried out in the presence of an oligonucleotide that has been labeled with an intercalator fluorescent pigment, wherein the sequence of said oligonucleotide is complementary to at least a portion of the sequence of the RNA transcription product and, in the situation where complementary binding of said oligonucleotide to said RNA transcription product occurs, the fluorescent properties of the reaction solution change in comparison with the situation where no complex is formed, whereby the detection can be carried out by measuring the fluorescent intensity of the reaction solution.

Figure 1:
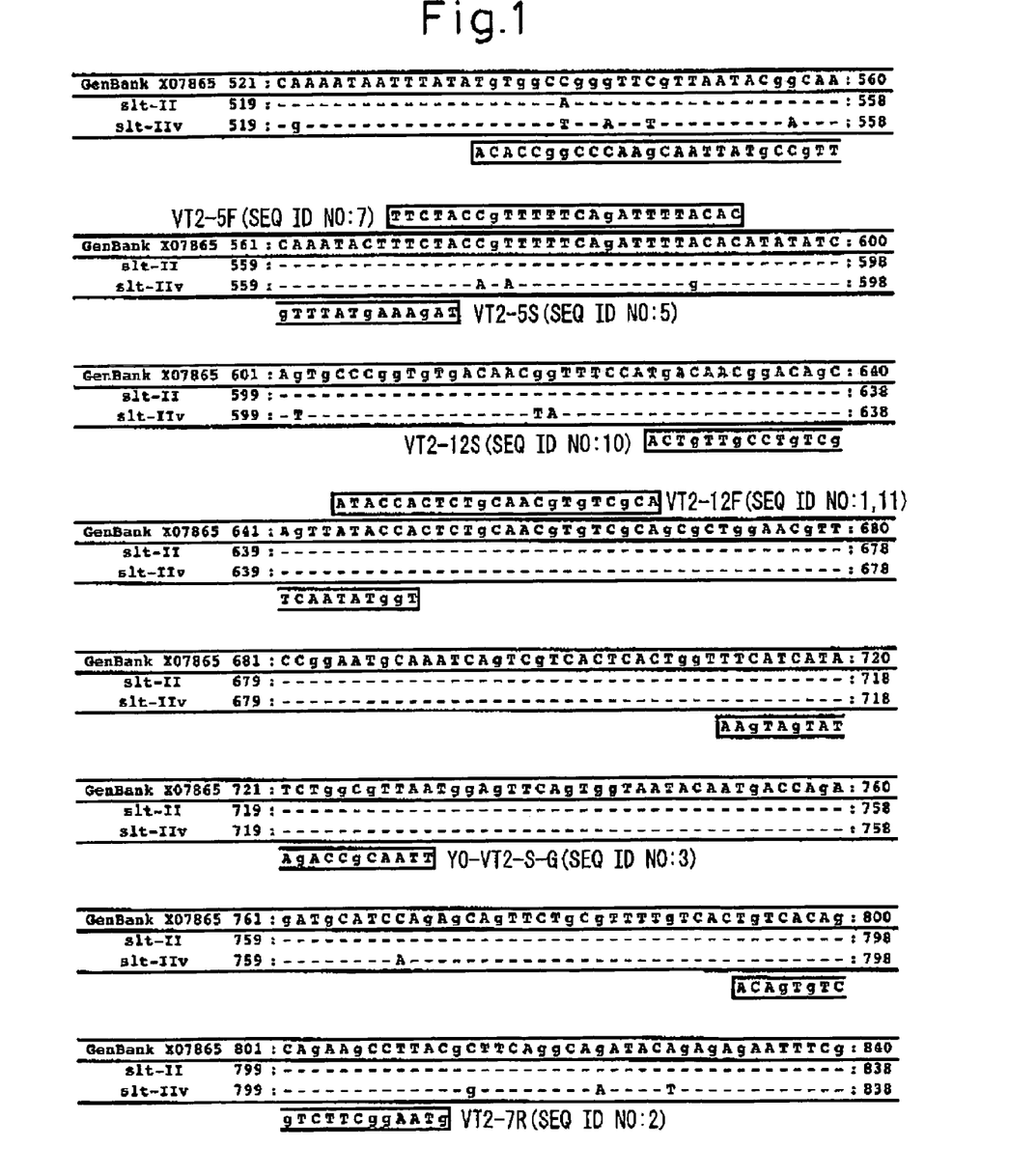
FIG. 1 shows the binding sites of each oligonucleotide for detecting stx2 RNA used in Example 1 and Example 2 along with the RNA amplification regions and their peripheral base sequences for three types of stx2 genes, SEQ ID NOS:12, 13, and 14 (see Ito et al., Microbial Pathogenesis 8, 47-60 (1990) and GenBank No. X07865). The sites indicated with a "-" in the base sequences indicate sites identical to the base sequence of GenBank No. X07865. All of the oligonucleotides used in the invention of the present application were designed on the basis of sites free of alterations between genotypes.

However, the aforementioned method has problems in terms of its sensitivity and speed. According to Japanese Unexamined Patent Publication No. 2002-253257, in the case where the initial amount of stx2 RNA is $10^2$ copies, the detection time is about 17 minutes, which is slower than the detection time with an stx1 RNA detection reagent ($10^2$ copies of stx1 RNA are detected in about 14 minutes) (see Example 1). In addition, the second primer of the aforementioned method may have a mismatch in the base sequence caused by a difference in the genotype, and EHEC carrying a genotype having a mismatch is thought to result in a slower detection time or be unable to be detected (refer to FIG. 1).

Therefore, the object of the present invention is to provide a detection reagent for stx2 RNA that has superior speed and specificity independent of differences in genotype.

As a result of extensive studies to develop a detection reagent for stx2 RNA of EHEC having a superior speed and specificity, the inventors of the present invention developed a reagent capable of solving the problem of mismatches (see FIG. 1) and detecting an initial amount of stx2 RNA of $10^2$ copies in about 14 minutes on the basis of designing oligonucleotides from sites where there is no alteration in the different genotypes.

The present invention relates to a detection reagent for use in detecting Shiga-toxin family gene type 2 (stx2) of entero-hemorrhagic *Escherichia coli* present in a sample that is used in a detection method using an RNA amplification process, comprising the steps of:

producing a cDNA with an RNA-dependent DNA polymerase using a specific sequence of an RNA derived from stx2 as a template, as well as a first primer having a sequence homologous to said specific sequence, and a second primer having a sequence complementary to said specific sequence, thereby forming a double-strand RNA-DNA, wherein either the first primer or the second primer has a sequence in which a promoter sequence of an RNA polymerase has been added to its 5' end;

degrading the RNA portion of said double-strand RNA-DNA by ribonuclease H, thereby producing a single-strand DNA; and producing a double-strand DNA having said promoter sequence capable of transcribing the RNA composed of the specific sequence of the RNA or the sequence complementary to said specific sequence of the RNA with a DNA-dependent DNA polymerase using said single-strand DNA as a template; wherein, the double-strand DNA produces an RNA transcription product in the presence of the RNA polymerase, and said RNA transcription product serves as a template for the subsequent cDNA synthesis with the RNA-dependent DNA polymerase;

which reagent comprises, as the first primer, an oligonucleotide consisting of at least 10 contiguous bases of the sequence shown in SEQ. ID No. 1, or an oligonucleotide in which one or more of the nucleotides in the oligonucleotide consisting of at least 10 contiguous bases shown in SEQ. ID No. 1 are deleted, substituted or added and is capable of specifically binding to the sequence complementary to the specific sequence, or an oligonucleotide that hybridizes under highly stringent conditions with the oligonucleotide consisting of at least 10 contiguous bases of the sequence shown in SEQ. ID No. 1 and is capable of specifically binding to the sequence complementary to the specific sequence; and as the second primer, an oligonucleotide consisting of at least 10 contiguous bases of the sequence shown in SEQ. ID No. 2, or an oligonucleotide in which one or more of the nucleotides in the oligonucleotide consisting of at least 10 contiguous bases shown in SEQ. ID No. 2 are deleted, substituted or added and is capable of specifically binding to said specific sequence, or an oligonucleotide that hybridizes under highly stringent conditions with the oligonucleotide consisting of at least 10 contiguous bases of the sequence shown in SEQ. ID No. 2 and is capable of specifically binding to said specific sequence.

The highly stringent conditions refer to any hybridization conditions and, for example, are those indicated in the following examples consisting of carrying out a hybridization at a temperature of 41° C. to 44° C. in the presence of 60 mM Tris, 17 mM magnesium chloride, 100-150 mM potassium chloride and 1 mM DTT.

Furthermore, in the case of intending to detect an RNA complementary to the RNA derived from stx2, an oligonucleotide having a sequence complementary to the aforementioned first primer with its sequence from the 5' end to the 3' end being reversed should be used as the first primer, and an oligonucleotide having a sequence complementary to the aforementioned second primer with its sequence from the 5' end to the 3' end being reversed should be used as the second primer.

Preferably, the aforementioned RNA amplification process is carried out in the presence of a cleaving oligonucleotide that cleaves the aforementioned target RNA at the 5' end of the aforementioned specific sequence and has a sequence complementary to the region adjacent to and overlapping with the 5' end of said specific sequence.

In a preferable aspect, the aforementioned first primer is an oligonucleotide of the sequence shown in SEQ. ID No. 1

In another preferable aspect, the aforementioned second primer is an oligonucleotide of the sequence shown in SEQ. ID No. 2.

In a more preferable aspect, the aforementioned first primer is an oligonucleotide of the sequence shown in SEQ. ID No. 1, and the aforementioned second primer is an oligonucleotide of the sequence shown in SEQ. ID No. 2.

In a still another preferable aspect, the aforementioned RNA amplification process is carried out in the presence of an oligonucleotide labeled with an intercalator fluorescent pigment, and the detection of EHEC is carried out by measuring the fluorescent intensity of the reaction solution. Here, the sequence of said oligonucleotide is complementary to at least a portion of the sequence of the RNA transcription product, and in the situation where complementary binding of said oligonucleotide to said RNA transcription product occurs, the fluorescent properties of the reaction solution change in comparison with the situation where no complex is formed.

Preferably, the aforementioned oligonucleotide labeled with an intercalator pigment consists of at least the 10 contiguous bases shown in SEQ. ID No. 3.

A detection method using the detection reagent of the invention of the present application is useful for detecting stx2 RNA of entero-hemorrhagic *Escherichia coli*, regardless of differences in genotype, more rapidly and with higher specificity than the method of the prior art (Japanese Unexamined Patent Publication No. 2002-253257).

BRIEF DESCRIPTION OF THE DRAWINGS

FIG. 2(A) shows a graph of the fluorescent intensity ratio that increases with the reaction time and the production of RNA, at an initial stx1 RNA amount of from $10^2$ copies/test to $10^5$ copies/test carried out in Example 1 (fluorescent intensity profile for stx1), and (B) shows a graph of the fluorescent intensity ratio that increases with the reaction time and the production of RNA, at an initial stx2 RNA amount of from $10^2$ copies/test to $10^5$ copies/test carried out in Example 1 (fluorescent intensity profile for stx2). "Nega" refers to a sample in which a diluent was used instead of an RNA sample. $10^2$ copies of stx1 RNA were detected in about 14 minutes, while $10^2$ copies of stx2 RNA were detected in about 17 minutes, and the detection time for stx2 RNA was indicated to be longer than the detection time for stx1 RNA.

FIG. 3(C) shows a calibration curve obtained between the logarithmic value of the initial RNA amount and the rise time at an initial stx1 RNA amount of from $10^2$ copies/test to $10^5$ copies/test carried out in Example 1 (calibration curve for stx1), and (D) shows a calibration curve obtained between the logarithmic value of the initial RNA amount and the rise time at an initial stx2 RNA amount of $10^2$ copies/test to $10^5$ copies/test carried out in Example 1 (calibration curve for stx2).

FIG. 4(A) shows a graph of the fluorescent intensity ratio that increases with the reaction time and the production of RNA, at an initial stx2 RNA amount of from $10^2$ copies/test to $10^5$ copies/test carried out in Example 2 (fluorescent intensity profile for stx2), and (B) shows a calibration curve obtained between the logarithmic value of the initial RNA amount and the rise time (calibration curve for stx2). "Nega" refers to a sample in which a diluent was used instead of an RNA sample. $10^2$ copies of stx2 RNA were detected in about 14 minutes, indicating a shorter detection time as compared with the method of the prior art (Japanese Unexamined Patent Publication No. 2002-253257).

The following provides a detailed explanation of the present invention.

BEST MODE FOR CARRYING OUT THE INVENTION

The following provides a detailed explanation of the present invention.

In the present invention, although the entire length of the base sequences listed in each of the sequence listings can be used for the first and second primers, respectively, as about 10 bases are sufficient for specific binding to a specific nucleic acid sequence or the like, a combination of oligonucleotides consisting of at least 10 contiguous bases in each sequence may also be used.

The amplification process of the present invention includes the NASBA method, 3SR method and the TRC method (see, e.g., Japanese Unexamined Patent Publication No. 2000-014400), which amplifies stx2 RNA sequence by the concerted action of reverse transcriptase and RNA polymerase (by reacting them under conditions where the reverse transcriptase and RNA polymerase act in concert). Here, although there are no particular limitations on temperature, it is preferably 35 to 50° C.

In one aspect of the aforementioned invention of the present application, it is necessary for a target RNA to be cleaved at the 5' end of a specific sequence. A preferable method for cleaving the target RNA in this manner consists of cleaving the target RNA with ribonuclease H or the like by adding an oligonucleotide having a sequence complementary to the region adjacent to and overlapping with the 5' end of the specific sequence (cleaving oligonucleotide). Here, the number of overlapping bases is particularly preferably 5 or 6 bases. In said cleaving oligonucleotide, the 3' end hydroxyl group is preferably chemically modified and, for example, may be aminated, in order to suppress an elongation reaction from the 3' end.

Although the amplification product obtained in the aforementioned nucleic acid amplification method can be detected with a known nucleic acid detection method, in a preferable aspect of this method, the aforementioned nucleic acid amplification is preferably carried out in the presence of an oligonucleotide labeled with an intercalator fluorescent pigment followed by measurement of the change in the fluorescent properties of the reaction solution. In said oligonucleotide, as the intercalator fluorescent pigment is bound to the phosphorous atom in the oligonucleotide by means of a linker, the intercalator portion that forms a double strand with the target nucleic acid (complementary nucleic acid) intercalates to the double strand portion resulting in a change in fluorescent properties, thereby resulting in the characteristic of not requiring separation and analysis (Ishiguro, T. et al. (1996) Nucleic Acid Res. 24 (24) 4992-4997).

The sequence bound by said oligonucleotide may be any sequence specific for stx2 RNA, and although there are no particular limitations thereon, a sequence consisting of at least 10 contiguous bases in the sequence shown in SEQ. ID No. 3 or its complementary sequence is preferable. In addition, the hydroxyl group at the 3' end of said oligonucleotide is preferably chemically modified to suppress the elongation reaction which may occur by using this oligonucleotide as a primer, and an example of this is the method described in Japanese Unexamined Patent Publication No. 2000-316587.

As a result, stx2 RNA of EHEC can be amplified and detected in a single tube, at a constant temperature and in a single step, rapidly and with high sensitivity, thereby facilitating application to automation.

EXAMPLES

Although the following provides a more detailed explanation of the invention of the present application through examples, the present invention is not limited by these examples.

Example 1

Various numbers of copies of stx1 RNA and stx2 RNA of entero-hemorrhagic *Escherichia coli* (EHEC) were detected using the combinations of oligonucleotides described in Japanese Unexamined Patent Publication No. 2002-253257.

(1) A sample of a standard RNA (1337 bases) comprising base numbers 228 through 1558 of stx1 RNA of EHEC (the base numbering of the RNA is in accordance with Calderwoods, et al., Proc. Natl. Acad. Sci. USA 84 (13), 4364-4368 (1997), GenBank No. M16625) was quantified by ultraviolet absorption at 260 nm, and then diluted with an RNA diluent (10 mM Tris-HCl buffer (pH 8.0), 1 mM EDTA, 5 mM DTT, 0.25 U/μL RNase inhibitor (Takara Bio)) from $10^5$ copies/5 μL to $10^2$ copies/5 μL. Only diluent was used for the control group (negative control).

(2) A sample of a standard RNA (1361 bases) comprising base numbers 125 through 1479 of stx2 RNA of EHEC (the base numbering of the RNA are in accordance with GenBank No. X07665) was quantified by ultraviolet absorption at 260 nm, and then diluted with an RNA diluent (10 mM Tris-HCl buffer (pH 8.0), 1 mM EDTA, 5 mM DTT, 0.25 U/μL RNase inhibitor (Takara Bio)) from $10^5$ copies/5 μL to $10^2$ copies/5 μL. Only diluent was used for the control group (negative control).

(3) 20 μL of a reaction solution having the composition indicated below were dispensed into 0.5 mL PCR tubes (GeneAmp Thin-Walled Reaction Tubes, Applied Biosystems) followed by the addition of 5 μL of the aforementioned RNA sample thereto. Furthermore, solutions were prepared so that the combinations of the first primer, the second primer, the cleaving oligonucleotide and the oligonucleotide labeled with intercalator pigment were combined as shown in Table 1.

Composition of Reaction Solution (concentrations are shown as the concentration in the final reaction solution volume of 30 μL)
  60 mM Tris-HCl buffer (pH 8.6)
  17 mm magnesium chloride
  100 mM potassium chloride (for stx1) or
  150 mM potassium chloride (for stx2)
  6 U RNase inhibitor
  1 mM DTT
  0.25 mM each of dATP, dCTP, dGTP and dTTP
  3.6 mM ITP
  3.0 mM each of ATP, CTP, GTP and UTP
  0.16 μM cleaving oligonucleotide
  1.0 μM second primer
  1.0 μM first primer
  25 nM oligonucleotide labeled with intercalator pigment
  13% DMSO
  Distilled water for adjusting volume (3) After incubating the aforementioned reaction solution at 44° C. (for stx1) or at 41° C. (for stx2) for 5 minutes, 5 μL of an enzyme solution having the composition indicated below and pre-heated for 2 minutes at 44° C. (for stx1) or 41° C. (for stx2) were added.

Composition of Enzyme Solution (values shown indicate the values for a final reaction solution volume of 30 μL)
  2.0% sorbitol
  3.6 μg bovine serum albumin
  142 U T7 RNA polymerase (Invitrogen)
  6.4 U AMV reverse transcriptase (LifeScience)
  Distilled water for adjusting volume (4) Subsequently, the reaction solution in each of the PCR tubes was measured, over time, at an excitation wavelength of 470 nm and fluorescent wavelength of 520 nm, while being incubated at 44° C. (for stx1) or 41° C. (for stx2), using a fluorescent spectrophotometer equipped with a temperature control function and capable of directly measuring the tube.

By setting the time of the addition of the enzyme as 0 min., the time-dependent changes in the fluorescent intensity ratio of the stx1 and stx2 samples (fluorescent intensity value at predetermined time÷background fluorescent intensity value) are shown in FIGS. 2(A) and 2(B). In addition, the results obtained for the relationship between the logarithmic value of the initial RNA amount and the "rise time" (the time required for the ratio in the fluorescence increase to reach 1.2 times the sum of the negative control sample's average value plus 3 standard deviations) are shown for the stx1 and stx2 samples in FIGS. 3(C) and 3(D). Furthermore, the initial RNA amount ranged from $10^2$ copies/test to $10^5$ copies/test for both stx1 and stx2.

Figure 2:
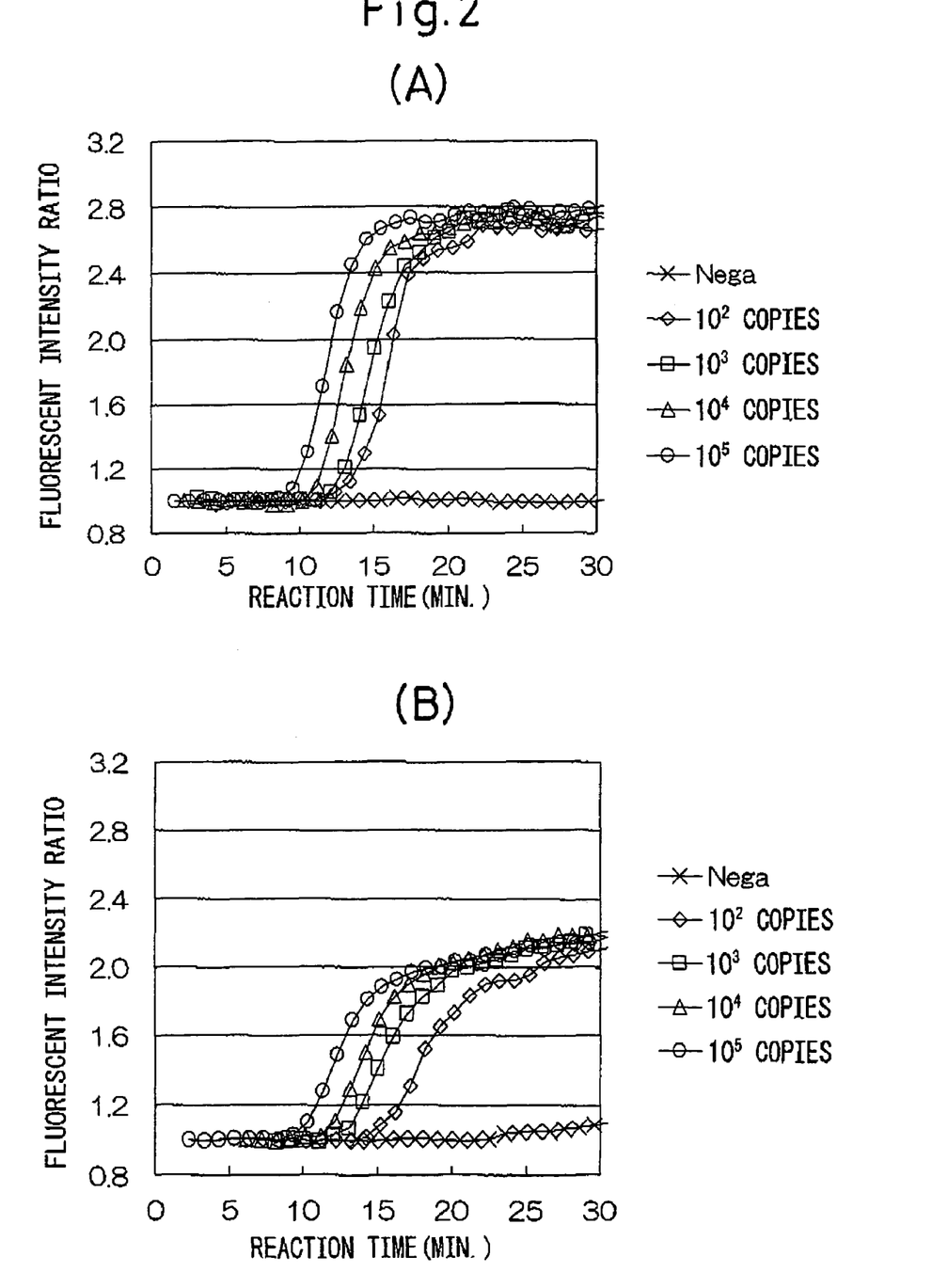
Figure 3:
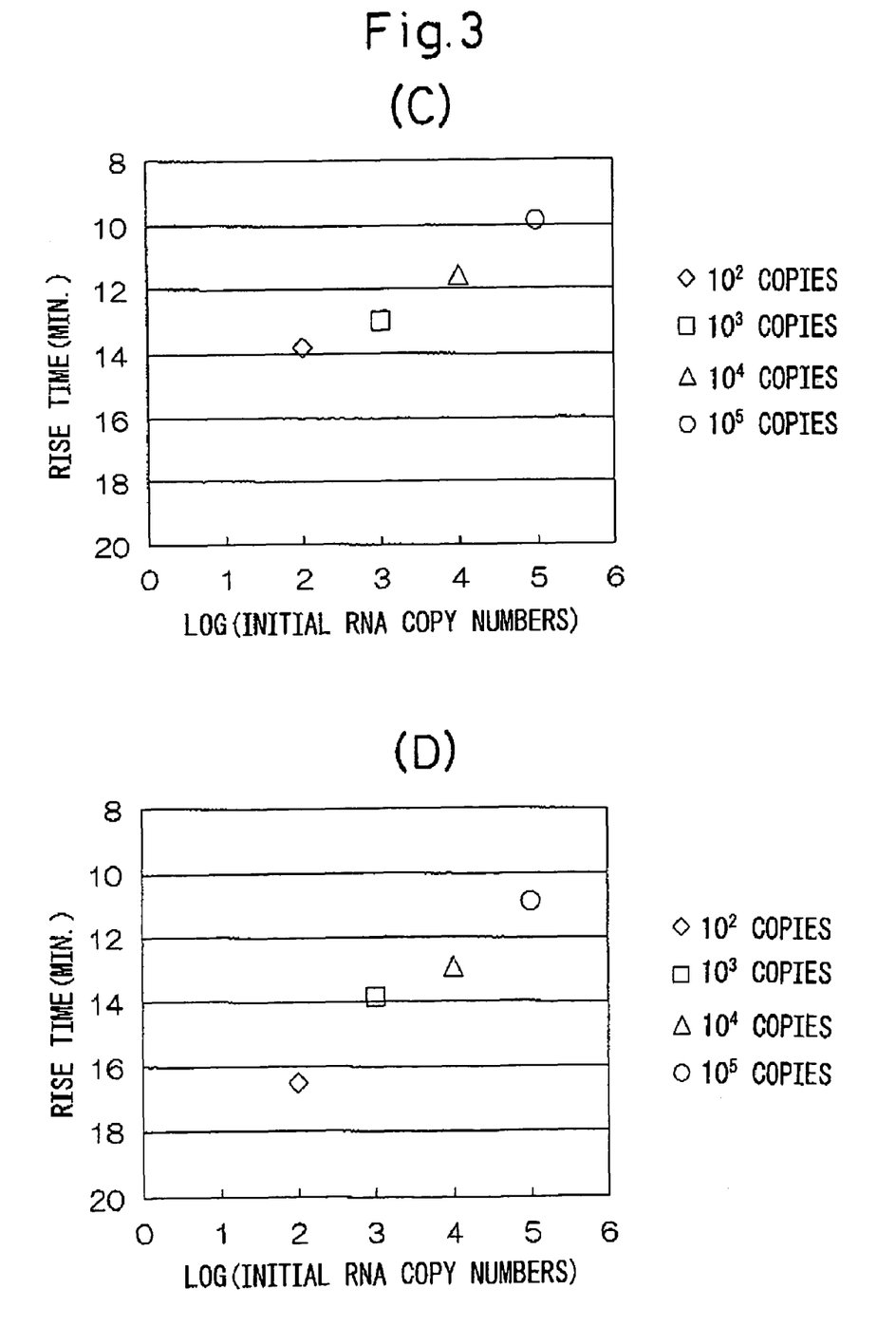

According to FIG. 2, $10^2$ copies of stx1 RNA were detected in about 14 minutes, and $10^2$ copies of stx2 RNA were detected in about 17 minutes. According to these results, the use of the combinations of oligonucleotides for detecting stx2 RNA described in Japanese Unexamined Patent Publication No. 2002-253257 demonstrated a slower detection time as compared with those for detection of stx1 RNA.

TABLE 1

| Combination | Cleaving oligo. | First primer | Second primer | Oligo. labeled with intercalator pigment |
|---|---|---|---|---|
| For stx1 RNA detection | VT1-5S | VT1-5F | VT1-6R | YO-VT1-S-G |
| For stx2 RNA detection | VT2-5S | VT2-5F | VR2-7R | YO-VT2-S-G |

Table 1 shows the combinations of the first primer, the second primer, the cleaving oligonucleotide and the oligonucleotide labeled with intercalator pigment used in the experimental system. The sites corresponding to the oligonucleotides in stx2 RNA of EHEC are shown for each of the oligonucleotide combinations for detection of stx2 in FIG. 1. The hydroxyl group on the 3' end of the base sequence of the cleaving oligonucleotide was aminated. The region from the 1st "A" to the 22nd "A" from the 5' end of the base sequence of the first primer is a T7 promoter region, and the subsequent region from the 23rd "G" to the 28th "A" is an enhancer sequence. The oligonucleotides labeled with intercalator pigment were labeled with intercalator pigment at the phosphorous atom between the 6th "C" and 7th "G" from the 5' end of YO-VT1-S-G (SEQ. ID No. 9), and between the 12th "T" and 13th "A" from the 5' end of YO-VT2-S-G (SEQ. ID No. 3), and the hydroxyl group on the 3' end was modified with a glycol group.

Cleaving oligonucleotides:
VT1-5S (SEQ. ID No. 4)
VT2-5S (SEQ. ID No. 5)
First Primers:
VT1-5F (SEQ. ID No. 6)
VT2-5F (SEQ. ID No. 7)
Second Primers:
VT1-6R (SEQ. ID No. 8)
VT2-7R (SEQ. ID No. 2)
Intercalator pigment-labeled oligonucleotides:
YO-VT1-S-G (SEQ. ID No. 9)
YO-VT2-S-G (SEQ. ID No. 3)

Example 2

Various initial numbers of copies of stx2 RNA of EHEC were detected using combinations of oligonucleotides of the invention of the present application.

(1) Similar to Example 1, stx2 RNA of EHEC was diluted from $10^5$ copies/5 μL to $10^2$ copies/5 μL with an RNA diluent (10 mM Tris-HCl (pH 8.0), 1 mM EDTA, 5 mM DTT, 0.25 U/μL RNase inhibitor (Takara Bio)). Only diluent was used for the control group (negative control).

(2) 20 μL of a reaction solution having the composition indicated below were dispensed into PCR tubes (volume: 0.5 mL, GeneAmp Thin-Walled Reaction Tubes, Applied Biosystems) followed by the addition of 5 μL of the aforementioned RNA sample thereto.

Composition of Reaction Solution (concentrations are shown as the concentration in the final reaction solution volume of 30 μL)
  60 mM Tris-HCl buffer (pH 8.6)
  18 mM magnesium chloride
  100 mM potassium chloride
  6 U RNase inhibitor
  1 mM DTT
  0.25 mM each of DATP, dCTP, dGTP and dTTP
  3.6 mM ITP
  3.0 mM each of ATP, CTP, GTP and UTP
  0.16 μM cleaving oligonucleotide (VT2-12S, SEQ. ID No.10; hydroxyl group of its 3' end is aminated)
  1.0 μM first primer (VR2-12F, SEQ. ID No. 11)
  1.0 μM second primer (VT2-7R, SEQ. ID No. 2)
  25 nM oligonucleotide labeled with intercalator pigment (YO-VT2-S-G, SEQ. ID. No. 3, labeled with the intercalator fluorescent pigment at the phosphorous atom between the 12th "T" and 13th "A" from the 5' end, and the hydroxyl group on its 3' end being modified with a glycol group.)
  13% DMSO
  Distilled water for adjusting volume (3) After incubating the aforementioned reaction solution at 43° C. for 5 minutes, 5 μL of an enzyme solution having the composition indicated below and pre-heated for 2 minutes at 43° C. were added.

Composition of Enzyme Solution (values shown indicate the values for a final reaction solution volume of 30 μL)
  2.0% sorbitol
  3.6 μg bovine serum albumin
  142 U T7 RNA polymerase (Invitrogen)
  6.4 U AMV reverse transcriptase (LifeScience)
  Distilled water for adjusting volume (4) Subsequently, the reaction solution in each of the PCR tubes was measured, over time, at an excitation wavelength of 470 nm and fluorescent wavelength of 520 nm, while being incubated at 43° C., using a fluorescent spectrophotometer equipped with a temperature control function and capable of directly measuring the tube.

By setting the time of the addition of the enzyme as 0 min., the time-dependent changes in the fluorescent intensity ratio of the samples (fluorescent intensity value at predetermined time÷background fluorescent intensity value) are shown in FIG. 4(A). In addition, the results obtained for the relationship between the logarithmic value of the initial RNA amount and the "rise time" (the time required for the ratio in the fluorescence increase to reach 1.2 times the sum of the negative control sample's average value plus 3 standard deviations) is shown in FIG. 4(B). Furthermore, the initial RNA amount ranged from $10^2$ copies/test to $10^5$ copies/test.

Figure 4:
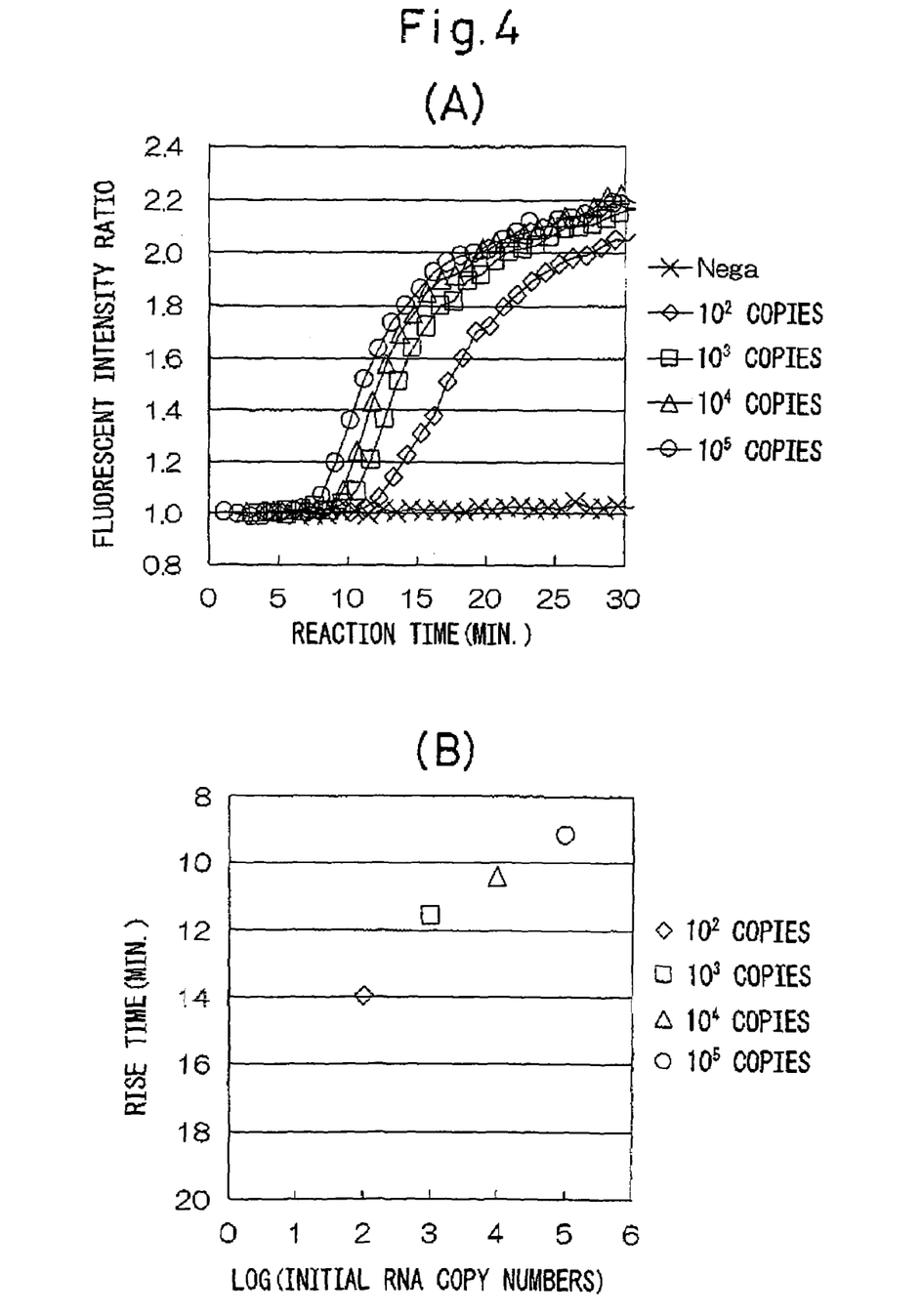

According to FIG. 4, $10^2$ copies were detected in about 14 minutes, demonstrating that detection is faster than methods of the prior art (Japanese Unexamined Patent Publication No. 2002-253257 and Example 1). In addition, since all of the oligonucleotides used in the invention of the present application are designed on the basis of the sites free of alterations between genotypes (see FIG. 1), the detection method of the invention of the present application is considered to be superior to the method of the prior art (Japanese Unexamined Patent Publication No. 2002-253257) with respect to specificity as well.

INDUSTRIAL APPLICABILITY

As has been explained above, the detection method of the invention of the present application is useful for detecting stx2 RNA of entero-hemorrhagic *Escherichia coli*, regardless of differences in genotype, more rapidly and with higher specificity than the method of the prior art (Japanese Unexamined Patent Publication No. 2002-253257).

The oligonucleotide of the invention of the present application is not limited to that of the base sequences listed in the sequence listings (having 20 to 23 bases), but rather can be a nucleotide comprised of at least 10 contiguous bases in those sequences. This is because it is clear that a base sequence of about 10 bases is sufficient for ensuring specificity to a target nucleic acid of a primer or probe under comparatively low-temperature (preferably 43° C.) conditions.

It will be appreciated by those skilled in the art that while the invention has been described above in connection with particular embodiments and examples, the invention is not necessarily so limited and that numerous other embodiments, examples, uses, modifications and departures from the embodiments, examples and use may be made without departing from the inventive scope of this application.

The invention claimed is:

1. A detection reagent for use in detecting the Shiga toxin family gene type 2 (stx2) of entero-hemorrhagic *Escherichia coli* present in a sample that is used in a detection method using an RNA amplification process comprising the steps of: producing a cDNA with an RNA-dependent DNA polymerase using a specific sequence of an RNA derived from stx2 as a template, as well as a first primer having a sequence homologous to said specific sequence, and a second primer having a sequence complementary to said specific sequence, thereby forming a double-strand RNA-DNA, wherein either the first primer or the second primer has a sequence in which a promoter sequence of an RNA polymerase has been added to its 5' end; degrading the RNA portion of said double-strand RNA-DNA by ribonuclease H, thereby producing a single-strand DNA; and producing a double-strand DNA having said promoter sequence capable of transcribing the RNA composed of the specific sequence of the RNA or the sequence complementary to said specific sequence of the RNA with a DNA-dependent DNA polymerase using said single-strand DNA as a template; wherein, the double-strand DNA produces an RNA transcription product in the presence of the RNA polymerase, and said RNA transcription product serves as a template for the subsequent cDNA synthesis with the RNA-dependent DNA polymerase; which reagent comprises, wherein the first primer is an oligonucleotide consisting of the sequence shown in SEQ. ID No. 1.

2. The detection reagent according to claim 1, wherein the RNA amplification process is carried out in the presence of an oligonucleotide that has been labeled with an intercalator fluorescent pigment, and the detection of the entero-hemorrhagic *Escherichia coli* is carried out by measuring the fluorescent intensity of the reaction solution; wherein the sequence of said oligonucleotide is complementary to at least a portion of the sequence of the RNA transcription product and, in the situation where complementary binding of said oligonucleotide to said RNA transcription product occurs, the fluorescent properties of the reaction solution change in comparison with the situation where no complex is formed.

3. A method of detecting a Shiga toxin family gene type 2 (stx2) of entero-hemorrhagic *Escherichia coli* present in a sample, comprising
producing a cDNA with an RNA-dependent DNA polymerase using a specific sequence of an RNA derived from stx2 as a template and the detection reagent according to claim 1, thereby forming a double-strand RNA-DNA, wherein either the first primer or the second primer in the detection reagent has a sequence in which a promoter sequence of an RNA polymerase has been added to its 5' end;
degrading the RNA portion of said double-strand RNA-DNA by ribonuclease H, thereby producing a single-strand DNA; and
producing a double-strand DNA having said promoter sequence capable of transcribing the RNA composed of the specific sequence of the RNA or the sequence complementary to said specific sequence of the RNA with a DNA-dependent DNA polymerase using said single-strand DNA as a template; wherein, the double-strand DNA produces an RNA transcription product in

SEQUENCE LISTING

```
<160> NUMBER OF SEQ ID NOS: 14

<210> SEQ ID NO 1
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 1
ataccactct gcaacgtgtc gca                                               23

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
gtaaggcttc tgctgtgaca                                                   20

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
ttaacgccag atatgatgaa                                                   20

<210> SEQ ID NO 4
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 4
aaaaaacatt atttgtcctg ttaacaaatc ctgtcacat                              39

<210> SEQ ID NO 5
<211> LENGTH: 39
<212> TYPE: DNA
<213> ORGANISM: Artificial Sequence
<220> FEATURE:
<223> OTHER INFORMATION: synthetic oligonucleotide
```

<400> SEQUENCE: 5
tagaaagtat tgttgccgt attaacgaac ccggccaca        39

<210> SEQ ID NO 6
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 6
aattctaata cgactcacta tagggagatt tttatcgctt tgctgatttt tca        53

<210> SEQ ID NO 7
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 7
aattctaata cgactcacta tagggagatt ctaccgtttt tcagatttta cac        53

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
tggcgattta tctgcatccc        20

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
tgtaacgtgg tatagctact        20

<210> SEQ ID NO 10
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 10
tggtataact gctgtccgtt gtca        24

<210> SEQ ID NO 11
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 11
aattctaata cgactcacta tagggagaat accactctgc aacgtgtcgc a        51

<210> SEQ ID NO 12

-continued

```
<211> LENGTH: 320
<212> TYPE: DNA
<213> ORGANISM: Escherichia coli

<400> SEQUENCE: 12
caaaataatt tatatgtggc cgggttcgtt aatacggcaa caaatacttt ctaccgtttt      60
tcagatttta cacatatatc agtgcccggt gtgacaacgg tttccatgac aacggacagc     120
agttatacca ctctgcaacg tgtcgcagcg ctggaacgtt ccggaatgca aatcagtcgt     180
cactcactgg tttcatcata tctggcgtta atggagttca gtggtaatac aatgaccaga     240
gatgcatcca gagcagttct gcgttttgtc actgtcacag cagaagcctt acgcttcagg     300
cagatacaga gagaatttcg                                                 320

<210> SEQ ID NO 13
<211> LENGTH: 320
<212> TYPE: DNA
<213> ORGANISM: Escherichia coli

<400> SEQUENCE: 13
caaaataatt tatatgtggc agggttcgtt aatacggcaa caaatacttt ctaccgtttt      60
tcagatttta cacatatatc agtgcccggt gtgacaacgg tttccatgac aacggacagc     120
agttatacca ctctgcaacg tgtcgcagcg ctggaacgtt ccggaatgca aatcagtcgt     180
cactcactgg tttcatcata tctggcgtta atggagttca gtggtaatac aatgaccaga     240
gatgcatcca gagcagttct gcgttttgtc actgtcacag cagaagcctt acgcttcagg     300
cagatacaga gagaatttcg                                                 320

<210> SEQ ID NO 14
<211> LENGTH: 320
<212> TYPE: DNA
<213> ORGANISM: Escherichia coli

<400> SEQUENCE: 14
cgaaataatt tatatgtggc tggatttgtt aatacgacaa caaatacttt ctacagattt      60
tcagattttg cacatatatc attgcccggt gtgacaacta tttccatgac aacggacagc     120
agttatacca ctctgcaacg tgtcgcagcg ctggaacgtt ccggaatgca aatcagtcgt     180
cactcactgg tttcatcata tctggcgtta atggagttca gtggtaatac aatgaccaga     240
gatgcatcaa gagcagttct gcgttttgtc actgtcacag cagaagcctt acgcttcagg     300
caaatactga gagaatttcg                                                 320
```